United States Patent
Hubbard

[11] Patent Number: 5,944,678
[45] Date of Patent: Aug. 31, 1999

[54] ANKLE BRACE

[76] Inventor: Craig John Hubbard, 20 Dover St., Red Hill, Brisbane 4059, Australia

[21] Appl. No.: 08/818,963

[22] Filed: Mar. 14, 1997

Related U.S. Application Data

[63] Continuation of application No. 08/428,246, filed as application No. PCT/AU93/00435, Aug. 27, 1993, abandoned.

[30] Foreign Application Priority Data

Aug. 27, 1992 [AU] Australia .................... PL 4320

[51] Int. Cl.⁶ ...................................................... A61F 5/00
[52] U.S. Cl. .............................................. 602/27; 602/65
[58] Field of Search .................... 602/5, 23, 27, 602/28, 29, 60, 61, 62, 65; 128/882, 892, 893

[56] References Cited

U.S. PATENT DOCUMENTS

| | | |
|---|---|---|
| 1,666,290 | 4/1928 | Johnston . |
| 1,837,488 | 12/1931 | Romero .................... 602/66 X |
| 4,495,942 | 1/1985 | Palumbo .................... 602/27 |
| 4,556,054 | 12/1985 | Paulseth . |
| 4,753,229 | 6/1988 | Sutherland . |
| 4,977,891 | 12/1990 | Grim . |
| 4,982,733 | 1/1991 | Broadhurst et al. . |
| 5,217,431 | 6/1993 | Toronto et al. . |

FOREIGN PATENT DOCUMENTS

| | | |
|---|---|---|
| 65560/90 | 5/1991 | Australia . |
| 183418 | 4/1907 | Germany . |
| WO 82/01659 | 5/1982 | WIPO . |
| WO 87/02885 | 5/1987 | WIPO . |
| WO 88/00033 | 1/1988 | WIPO . |
| WO 88/09156 | 12/1988 | WIPO . |
| WO 89/10111 | 11/1989 | WIPO . |
| WO 93/06797 | 4/1993 | WIPO . |

Primary Examiner—Richard J. Apley
Assistant Examiner—Kim M. Lee
Attorney, Agent, or Firm—Barnes & Thornburg

[57] ABSTRACT

An ankle brace having an upper portion adapted to extend about a wearer's ankle above a malleoli. The upper portion having at least one anchor site. A foot section conforming to a portion of a sole of the wearer's foot and an elastic lateral connection extending between the foot section and the upper portion enabling normal range of movement of the ankle and becoming increasingly taut at about the limit of either the normal or a preset range of movement. The anchor site having a pad with holes to which the skin of the foot conforms so as to adhere the pad to the skin. Suction cups and adhesive may also be used alternatively or in combination to adhere the pad to the skin of the wearer's foot.

40 Claims, 7 Drawing Sheets

Fig. 11.
(EXTERIOR)

ANKLE BRACE

This application is a continuation, of application Ser. No. 08/428,246 filed Apr. 27, 1995, now abandoned, which is a 371 of PCT AU93/00435, filed Aug. 27, 1993.

FIELD OF THE INVENTION

THIS INVENTION relates to an improved ankle brace.

BACKGROUND OF THE INVENTION

In particular the invention relates to an improved brace for externally supporting and protecting the human ankle and subtalar joints from injury or re-injured during recreational pursuits or in correction or rehabilitation of pathological or congenital malalignments and injury. The invention also relates to improvements in a reusable external prophylactic support or brace for the human ankle joint.

A number of techniques and devices have been proposed by which ankle injury might be minimized or prevented. Before these techniques and devices can be discussed it is useful in first discussing the anatomy of the ankle.

The ankle and foot complex consists of twenty-eight bones including the tibia and fibula. This specification will deal primarily with the six bones which comprise the ankle, subtalar, and transverse tarsal joints.

The complex interactions between bones, ligaments, tendons and their musculature enable the foot to transfer from a mobile adaptor during ground interface to a rigid lever for propulsion. The body requires a flexible foot to accommodate the variations in the external environment, a semi-rigid foot that can act as a spring or lever arm for push off during gait and a rigid foot to enable body weight to be carried with adequate stability. The position of the subtalar joint is the major factor in this adaptation. Eversion of the calcaneus results in pronation of the subtalar joint which in turn "unlocks" the transverse tarsal joint-whilst inversion leads to supination of the subtalar joint which in turn "locks" the transverse tarsal joint creating a rigid forefoot. A thorough understanding of the interrelation between joint axes and planes of motion is essential to analysis of compensatory motion as a consequence of pathological or restricted motion.

The bones of the foot interlock to form three distinct arches. The medial and lateral longitudinal arches and the transverse arch. The formation of these arches allows the support of body weight with the least expenditure of anatomical material and provides protection of the nerves and vasculature of the plantar foot. The bones of the medial arch are passively interlocked by the plantar aponeurosis, the long and short plantar ligaments, and the plantar calcaneonavicular (spring) ligament. During weight bearing, and heel raise, tension is increased especially in the plantar aponeurosis as the metatarsophalangeal joint extends adding stability.

The shape of the articular surfaces is particularly important to the evaluation of components of joint motions. Ligaments guide and check excessive joint motion with fiber direction determining what motions are guided and limited. The dorsal surface of the talus is called the trochlea. It is convex anterior-posterior, and convex-concave-convex medial to lateral. The trochlea has been described as a section of a cone with its base on the medial side. This surface articulates with the reciprocally shaped distal tibia. The lateral aspect of the talus is flat and is directed slightly medially from anterior to posterior and articulates with a reciprocally shaped distal fibula. The talus is slightly wider anteriorly than posteriorly.

The distal tibiofibula joint forms a deepened joint called the ankle mortise. The ligaments which stabilize the ankle consist of the strong medial ligament, and the three bands of the lateral ligament, together with the lateral malleolus provide lateral stability to the ankle joint and stabilize the talus within the ankle mortise.

Rotary stability in a horizontal plane is provided by tension in the collateral ligaments, by compression of the talar facets against the malleoli and, in the loaded state, by the shape of the articular surfaces. The horizontal components of tension in the collateral ligaments form a ring resisting rotation by tension in opposing pairs. The primary function of the malleoli as far as stability is concerned, is to serve as pillars so that the collateral ligaments are close to the ankle axis and hence permit plantar-dorsiflexion. Rotary instability may be an additional factor in patients whose symptoms persist after injury to the lateral ligaments.

The transverse tarsal joint exhibits triplanar motion and consists of the talonavicular and calcaneocuboid joints. Motion perpendicular to the two axes may be independent of each other, but both are dependent upon the position of the subtalar joint.

The calcaneocuboid axis lies close to the longitudinal axis and is directed anteriorly and superiorly 15 degrees to the horizontal and 9 degrees to the longitudinal, whilst the calcaneonavicular joint is oblique, directed anteriorly and superiorly at 52 degrees to the horizontal and medially at 57 degrees to the longitudinal axis.

During activity, as a person lands from a jump, the ankle is plantar flexed. The three lateral ligaments and peroneal muscle provide the primary restraints to ankle inversion. As inversion proceeds and the strength of the peroneal muscle is overcome, injury to the lateral ligaments will occur as the range of motion of the talus in the ankle mortis is exceeded.

Injury to the lateral ligaments occurs in a progressive fashion. The anterior talofibular ligament being the first to be injured. If inversion continues the calcaneofibular ligament is the next to be injured and finally, in severe cases, the posterior talofibular ligament is torn. The other mechanism of ankle injury is eversion. Eversion injury is more severe than inversion injury and may lead to chronic ankle instability.

Previous devices such as taping strapping and semi-rigid orthosis have been proposed for supporting these joints by rigidly (or semi-rigidly) inhibiting motion in the direction of possible injury. The ankle is prone to the following types of injury: inversion, eversion, dorsi flexion sprains and plantar flexion sprains.

Strapping of the ankle has been used to support the ankle. This involves taping of the ankle with non-elastic adhesive tape. Cloth wraps, elastic wraps and elastic adhesive materials have also been used. Whether taping, regardless of material used, is effective is debatable. Tape initially provides restriction of motion but this diminishes as exercise progresses. Taping is effective in preventing ankle sprains. Tape is not reusable and for taping to be effective the ankle may need to be retaped which involves unwinding and re-winding of the tape which is time consuming and expensive.

Ankle supports or braces which are re-usable have attempted to support the ankle by rigidly or semi-rigidly inhibiting motion in the direction of possible injury.

Australian patent specifications 19364/88 and 65560/90 are typical of such earlier braces or supports. These devices generally attempt to prevent ankle injury by restricting the range of movement of the ankle and, because of their rigid construction the degree of restriction provided by these devices does not change significantly following exercise.

Also typical of earlier devices are those disclosed in U.S. Pat. Nos. 4556054, 4982733, 1666290, 4977891 and 4753229.

It is an object of the present invention to provide an ankle brace which at least minimizes the disadvantages referred to above.

DISCLOSURE OF THE INVENTION

According to one aspect of the invention, there is provided an ankle brace having an upper portion adapted to extend about a wearer's ankle adjacent the malleoli, the upper portion having at least one anchor site, a foot section conforming to a portion of the sole of the wearer's foot and at least one elastic lateral connection extending between the foot section and the upper portion enabling normal range of movement of the ankle and becoming increasingly taut at about the limit of the normal or a preset range of movement.

Preferably the brace includes at least one elastic medial connection extending between the foot section and the upper portion of the brace. The elastic medial connection enables normal range of movement of the ankle and becomes increasingly taut at or about the limit of the normal or a preset range of movement.

Preferably the brace includes a medial anchor site on the upper portion of the brace and a lateral anchor site.

Preferably the ankle brace includes an adjustable inversion limiting connection extending from the foot section from an anterior lateral position adjacent the cuboid of the foot, across the outside of the ankle joint to the medial anchor site. The inversion limiting connection assists the medial and lateral connections in determining a safe active range of motion of the ankle.

The foot section preferably includes an outer fabric or skin. The outer fabric or skin may comprise a strong synthetic or natural fibre cloth. Preferably a strong synthetic cloth is employed. The synthetic may be nylon or any other suitable material such as neoprene. An inner fabric of like or dissimilar material may also be present. The foot section may include a foot insert. The foot insert may be moulded or contoured to conform to the contour of the wearer's foot. Preferably a thermosetting semi-rigid foot insert is employed. The insert is preferably semi-rigid at 20–60° C. and moldable to shape between 60–90° C. The foot insert functions to form an exo-skeleton around the foot and maintains form and restricts displacement of the foot within the brace to effectively transfer the forces of extreme or severe motion through the lateral and medial connections to the medial and lateral anchor sites in the upper portion of the brace. The insert has the effect at its medial and lateral borders of forming a broader and less flexible border to which the resistive/protective torques may be transferred via the exo-skeleton to the foot by the inversion limiting connection and talar stabilizing connections and the connections between the foot section and the upper portion.

The insert may have a comfort lining of suitable material. A thin layer of neoprene may be used. The layer may be about 2 mm thick. The insert together with the comfort lining may be positioned between the outer fabric and a similar inner fabric of the brace through an opening. The opening may be at an inferior anterior border of the brace.

The insert preferably has a reduced width at its lateral border so that it may extend beneath the lateral malleolus then expand across the instep to beneath the medial malleolus and more anteriorly to a location approximately over the talo-navicular joint. The narrow lateral boarder corresponds to the area of lowest loading during running and walking and is situated between the inferior posterior calcaneus and the proximal head of the fifth metatarsal. Expansion of the width of the insert over the instep may assist in protecting the foot against excessive pronation whilst assisting to maintain the integrity of the longitudinal arch during its role in shock absorption in locomotion. Preferably the insert is perforated to reduce weight and allow perspiration to dissipate.

The upper portion of the brace may completely encircle the foot. Preferably at least a posterior or anterior portion of the upper portion is elastic and adjustable to enable the wearer's foot to be inserted into the brace. In one embodiment at least the anterior portion is made of or incorporates elastic material for this purpose. Alternatively, the upper portion is open at either an anterior or posterior location and at least one adjustable connection is employed to close the opening at the anterior or posterior location after the foot has been inserted into the brace. More preferably an inferior and a superior connection are present both at the anterior and posterior portion of the upper portion to enable that portion to be closed about the wearer's foot. Preferably the connections are adjustable. The connections may comprise straps or buckles.

As mentioned, the brace has at least one elastic connection extending between the foot section and the upper portion of the brace. The connection may include lateral and medial connections and these connections may comprise straps. Preferably the or each lateral strap is adjustable. It is particularly preferred that two lateral straps be present and that one be spaced anteriorly of the other.

The lateral straps are preferably extensible and have an elastic limit greater than or at least equal to the force created by sudden inversion of the ankle. The lateral straps may have fixotropic characteristics in that the greater the rate of extension the more force is required to achieve further extension.

In one embodiment the straps comprise urethane strips about 1 cm wide, 2 cm long or may be ingot shaped with a middle section 1×2 mm. Alternatively, the strips may comprise a single strain rate material such as urethane encased in a sealed jacket filled with a fixotropic material.

The ends of the strips should increase in cross section to facilitate attachment to the upper portion and the foot section between which they extend.

The or each elastic medial connection may be constructed in a like way to the or each elastic lateral connection and may also comprise a strap.

Preferably, the brace also includes at least one elastic adjustable talar stabilizing connections. These connections comprise a medial and a lateral talar stabilizing connection. The talar connections extend from a posterior portion of the foot section, cross over each other in the region of the Achilles tendon and to opposite superior sides of the ankle terminating at anchor sites on the medial and lateral sides of the upper portion.

The talar stabilizing connections are preferably straps and preset the degree of talar tilt. These straps protect the calcaneo-fibula ligament from injury. The medial and lateral talar stabilizing straps provide a non-rigid control over rear foot motion by crossing the ankle at the Achilles tendon and attaching on opposite sides to their inferior origins to lateral and medial anchor sites.

The degree of talar tilt may be preset with mild elastic tension provided by the talar stabilizing straps and thus enables alignment of the rear foot for heel strike or such while still allowing supination-pronation during gait. The talar stabilizing straps may be constructed in a similar fashion to the inversion limiting strap but preferably have less hardness/unit length extension than the inversion limiting strap. The talar stabilizing straps preferably have a determinable amount of extension restricted by the strength of the material, of the brace when at full extension. The talar connections, as mentioned, are elastic and once a predetermined extension has been achieved corresponding to normal range of movement become increasingly taut. Adjustability of the straps may be achieved at their connection to the anchor sites or at some location along the length of the connection.

The adjustable inversion limiting connection is preferably a strap which does not restrict the natural motion of the foot since only minimal extension occurs during natural motion. The strap preferably has a rigid end point when fully extended. The strength of the material of construction of the brace provides support at this point. The strap preferably has a predetermined elastic limit. As the foot turns into inversion, the strap extends providing upward resistance to motion in that direction. When full (pre-set) extension is reached the rigid end point protects the ankle from further motion in that plane. Any force remaining is then transferred to the medial anchor site. This complements the energy transfer via the elastic connections between the upper portion and foot section of the brace.

The rigid end point proposed will only then transfer forces that were not transferred to the medial and lateral anchor sites to the elastic connections between the upper portion and foot section.

The adjustable nature of the inversion limiting strap serves several functions:
1. control of fore-foot alignment with non-rigid support;
2. limit the extent of inversion for controlled rehabilitation;
3. quick and easy to adjust;
4. decrease impulse of inversion loading and transfer same forces to the lower leg.

The strap when combined with the lateral talar stabilizing connection, when extended, protects the lateral ligaments from injury from any remaining forces. By presetting these so that they are fully extended at the limit of natural motion, injury to these ligaments can be prevented.

The anchor sites are located above each malleoli and preferably below the inferior border of the triceps surae (calf) muscle. Those parts of the brace spaced from the anchor sites and in contact with the skin are preferably adhered to the skin of the foot by employing an adhesive, evacuated air pressure or skin conformity or any combination of these. In one embodiment those portions of the brace are provided with a pad having a plurality of "sucker pads" or suction caps. The pads may be disposable and made of organic material such as paper or fiberboard. Alternatively, foam or silicon material may be used although other materials which are semi-rigid and maintains its shape and conform to the skin while being flexible enough to maintain conformity without causing damage or discomfort to the skin may also be used. It is preferred that the anchor sites be rounded in shape.

DISCLOSURE OF THE DRAWINGS

A particular preferred embodiment of the invention will now be described with reference to the drawings in which.

DETAILED DESCRIPTION OF THE DRAWINGS

Figure 1:
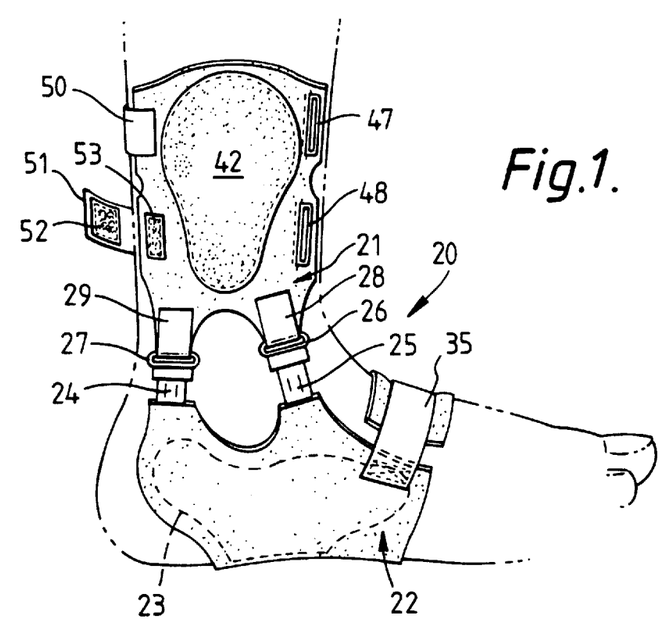
FIG. 1 is lateral view of the brace with some parts omitted for the sake of clarity.
Figure 2:
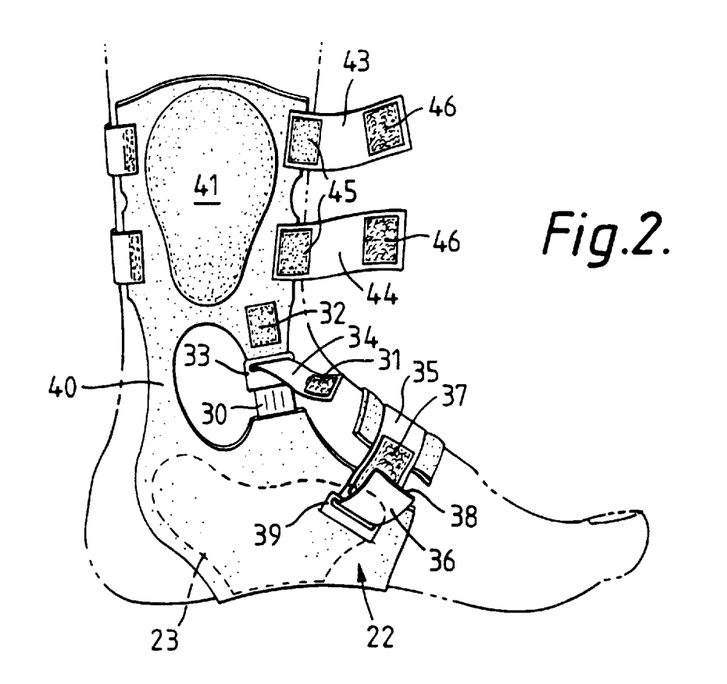
FIG. 2 is a medial view of the brace of FIG. 1.

The brace 20 has an upper portion 21 and a foot section 22 as shown in FIGS. 1 and 2. The foot section has a foot insert 23 located between inner and outer linings of the material from which the brace is constructed.

The foot section 22 is coupled to upper portion 21 by lateral straps 24 and 25 of elastic material. Straps 24, 25 terminate in eyelets 26, 27 for receiving strap portions 28, 29 which pass through the eyelets and attach to themselves via a press-on/tear-off fastening material such as VELCRO (trade mark).

Medial strap 30 of elastic material terminates in an eyelet for receiving strap portion 34 which in turn passes through the eyelet and is secured to itself via VELCRO fastener 31, 32.

Strap 35 extends over the foot from the lateral to the medial side and terminates in a strap portion 36 provided with VELCRO material 37, 38. Portion 36 passes through eyelet 39 on the medial side and then attaches to itself over the foot. A connecting portion 40 located posteriorly of strap 30 bridges between the upper portion 21 and the foot section 22 of the brace 20.

In this embodiment the medial anchor site 41 and the lateral anchor site 42 are visible. Adjacent the sites 41, 42 and anteriorly thereof are straps 43, 44 having VELCRO material 45, 46. Straps 43, 44 pass through eyelets 47, 48 to fix the anterior parts of the upper portion to each other. The posterior parts of the upper portion have straps 50, 51 which have VELCRO material 52 for attachment to VELCRO material 53 to attach the posterior parts to each other to close off the posterior of the upper portion.

Figure 5:
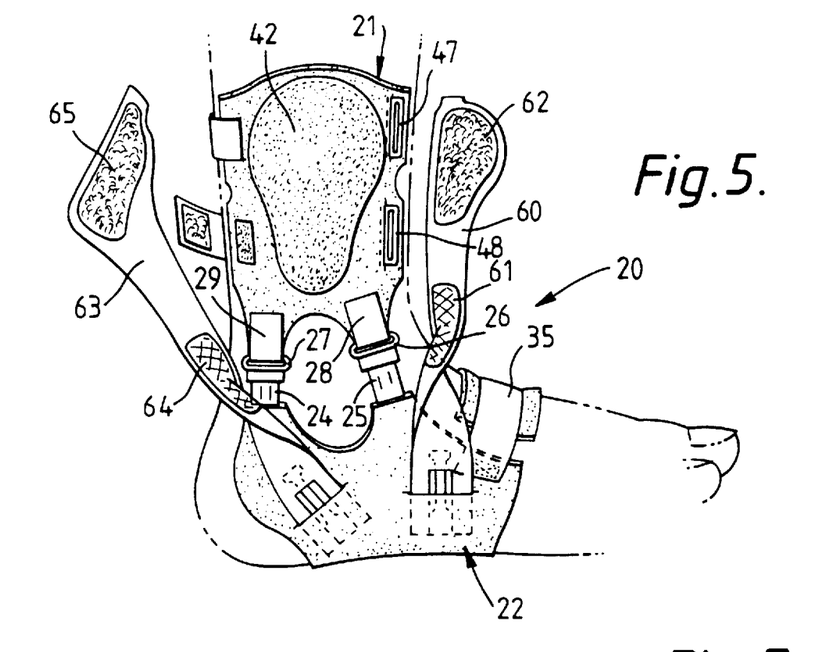
FIG. 5 is a lateral view of the brace prior to the attachment of the inversion limiting and talar stabilizing straps to the anchor sites.

FIG. 5 shows detail of the manner in which the adjustable inversion limiting strap 60 extends from the foot section 22 before attachment to the medial anchor site 41. The strap 60 has a comfort pad 61, typically of neoprene, on its inner face. VELCRO material 62 enables the free end of the strap to attach to site 41.

The lateral talar stabilizing strap 63 extends from the foot section 22 and has a comfort pad 64. The distal end of the strap 63 has VELCRO material 65 for attachment to site 41. The medial talar strap is not visible in this figure. The manner in which straps 60 and 63 attach to site 41 is best seen in FIG. 3.

Figure 3:
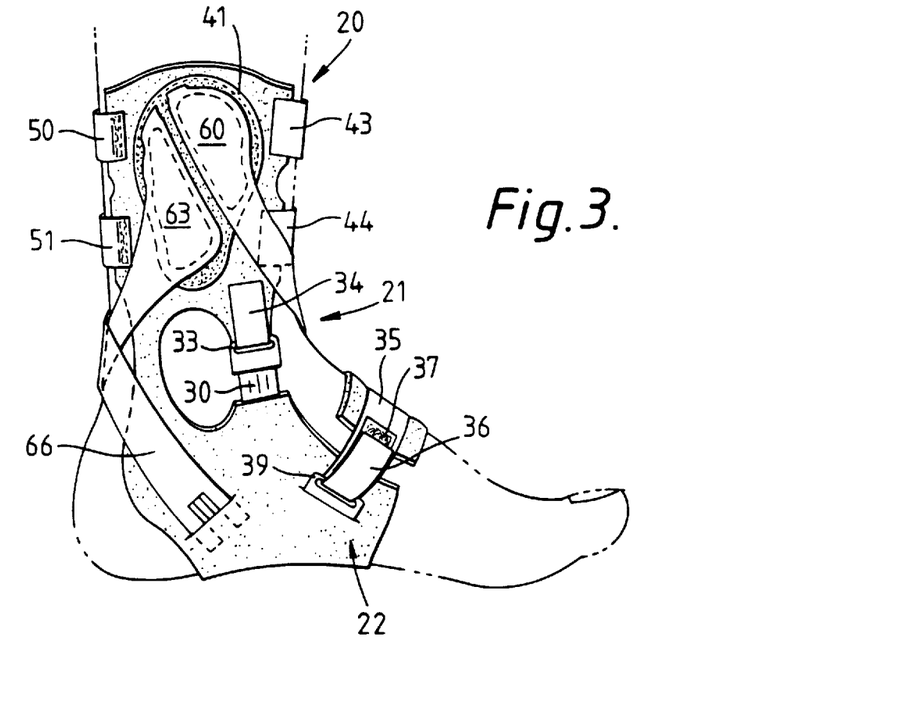
FIG. 3 is a medial view of the brace in which the adjustable inversion limiting and talar stabilizing straps are visible.
Figure 4:
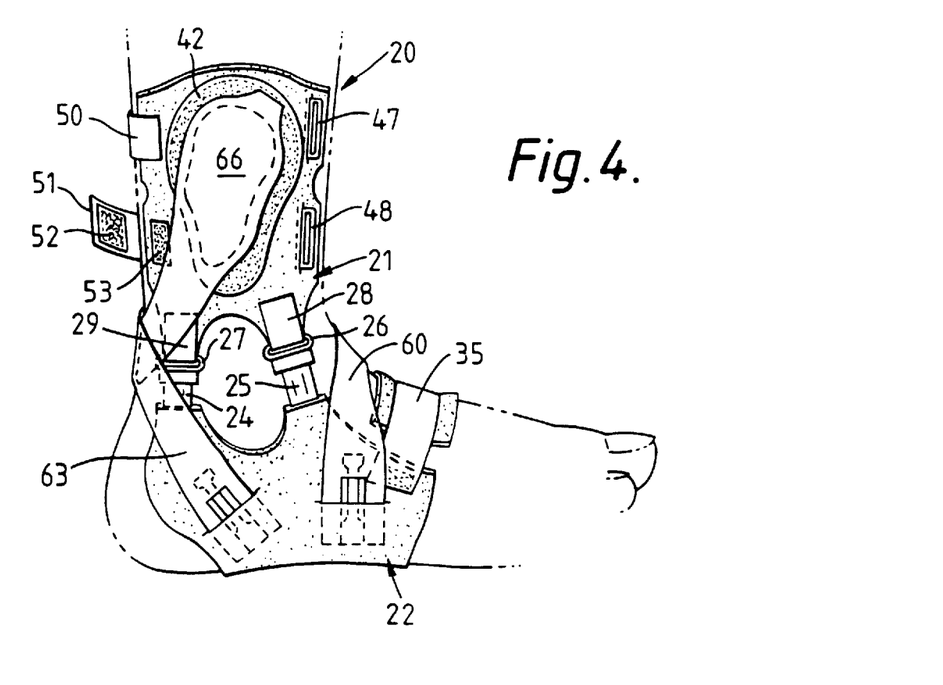
FIG. 4 is a lateral view of the brace of FIG. 3.

FIGS. 3 and 4 show detail of the medial talar strap 66 extends from the foot section 22 and attaches to site 42. Strap 66 also has a comfort pad (not shown).

Figure 6:
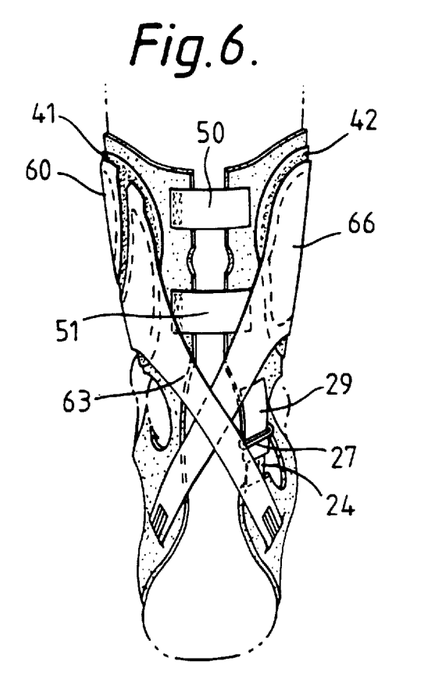
FIG. 6 is a posterior view of the brace.

FIG. 6 shows the way in which the lateral strap 63 and the medial strap 66 cross over in the region of the Achilles tendon and attach to the medial and lateral anchor sites 41, 42.

Figure 7:
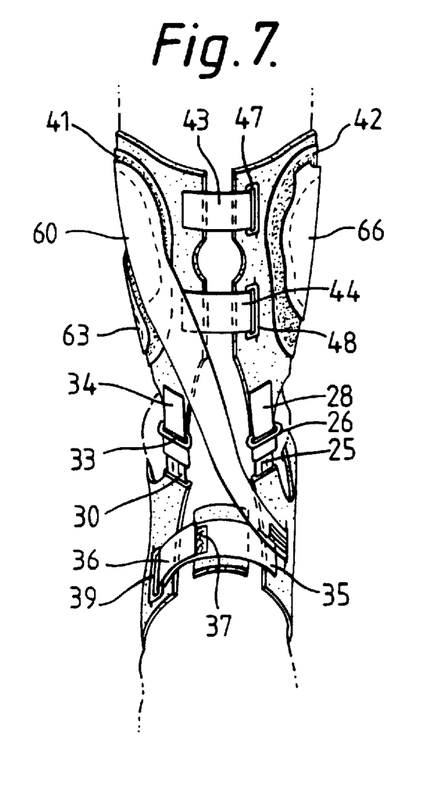
FIG. 7 is an anterior view of the brace.

FIG. 7 shows how the strap 60 extends from the foot section and across the anterior of the foot and attaches to the medial anchor site 41.

Figure 8A:
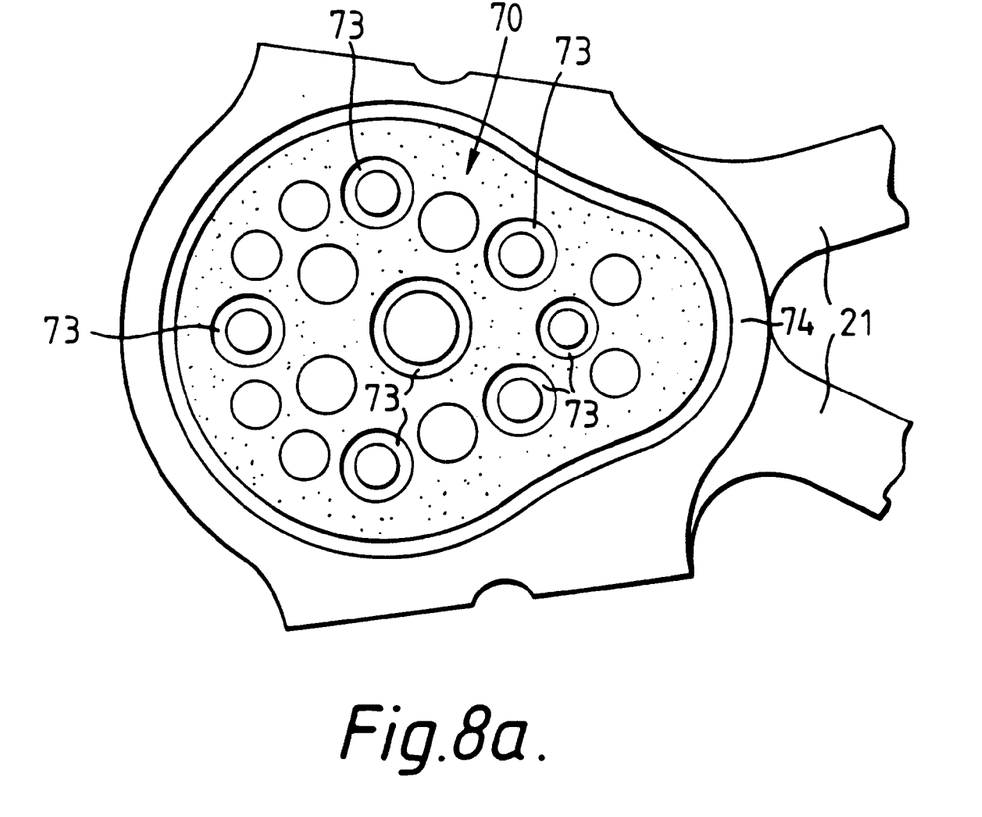
FIGS. 8a and 8b are inverted plan and sectional views of an anchor site.
Figure 8B:
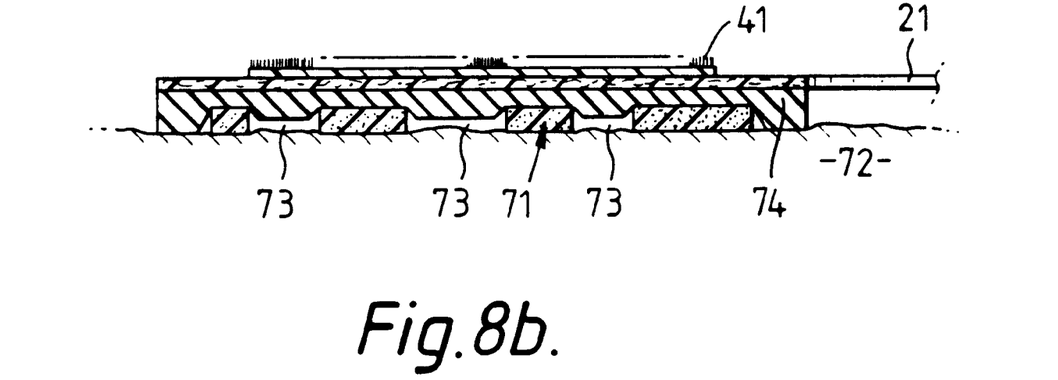

FIGS. 8a and 8b show views of a pad 70 which may be secured to the inner face of the upper portion 21 of the brace in the region of the anchor sites.

The inversion limiting strap, the talar stabilizing strap and the medial and lateral straps extending between the foot section and the upper portion may all have fixitrophic properties in that the greater the rate of extension the more force is required to achieve further extension. This property may be evident at the limit of normal range of movement.

The pad 70 includes a removable anchor pad 71 which may have a mild adhesive applied to it so that good contact is made with the skin 72. The pad 71 has a series of cups 73 which allow the skin to conform into them and hence increase shear force holding. Pad 71 is carried by a base 74 of urethane or silicon material which in turn is secured to the inner face of portion 21. The anchor site 41 with VELCRO material is shown.

Figure 9A:
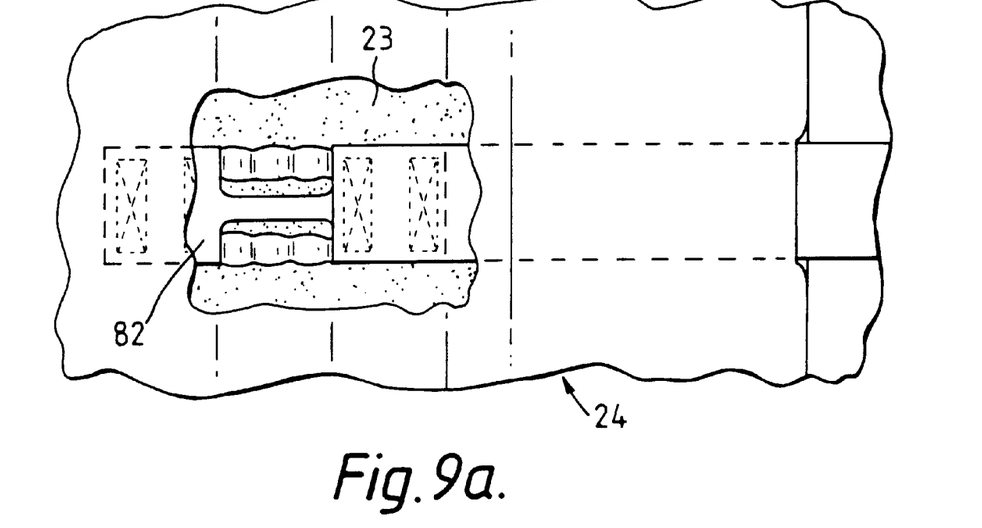
FIGS. 9a, 9b and 9c are face views and sectional views of a portion of the brace adjacent the foot insert.
Figure 9B:
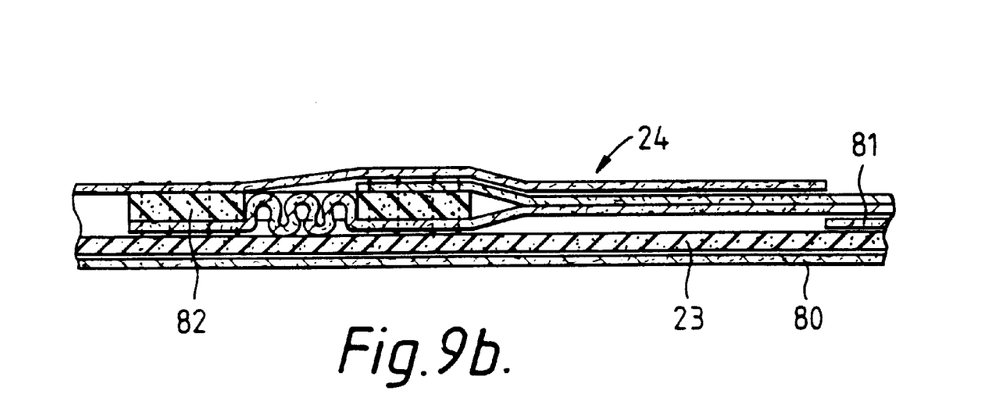
Figure 9C:
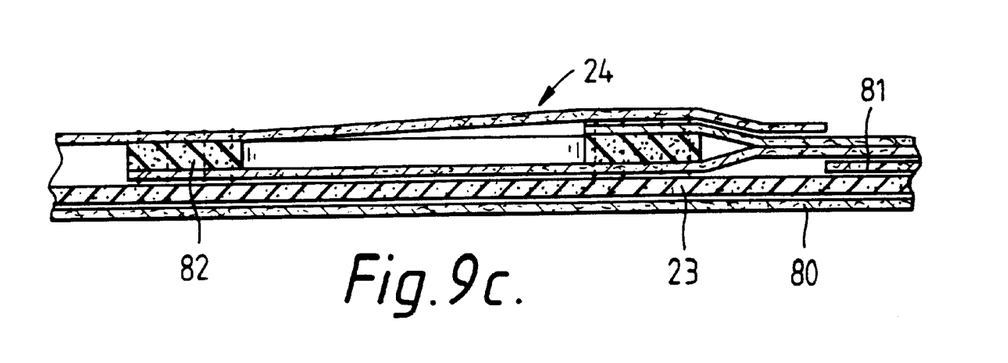

FIGS. 9a, 9b and 9c show views of the foot section with insert 23 positioned between inner and outer fabrics 80, 81 of the brace. Ingot shaped urethane material 82 which forms part of the one of the elastic straps 24 extending between the foot section 22 and the upper portion 21 of the brace 2.

Figure 10:
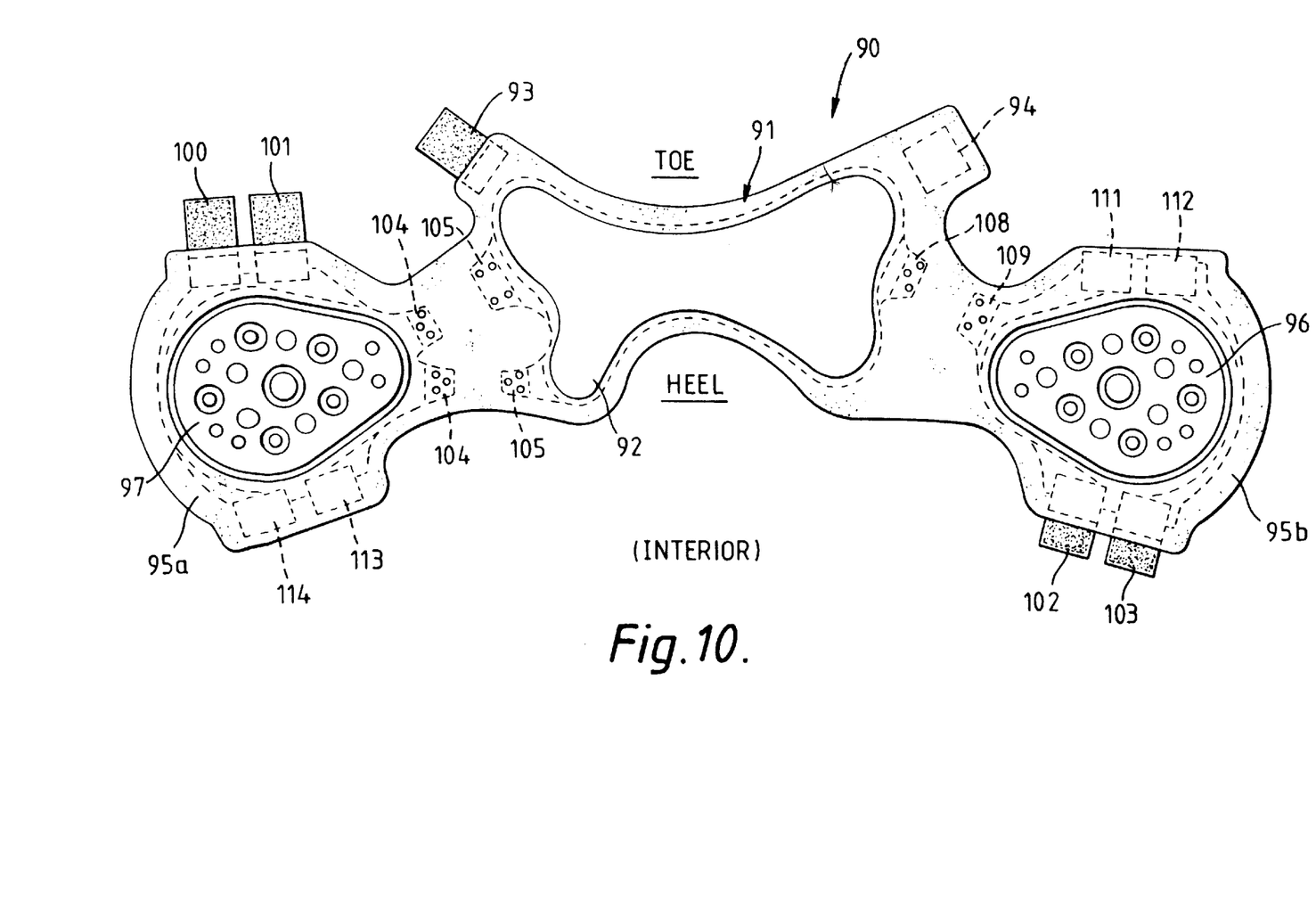
FIG. 10 is a view of the interior of an ankle brace according to another embodiment of the invention.
Figure 11:
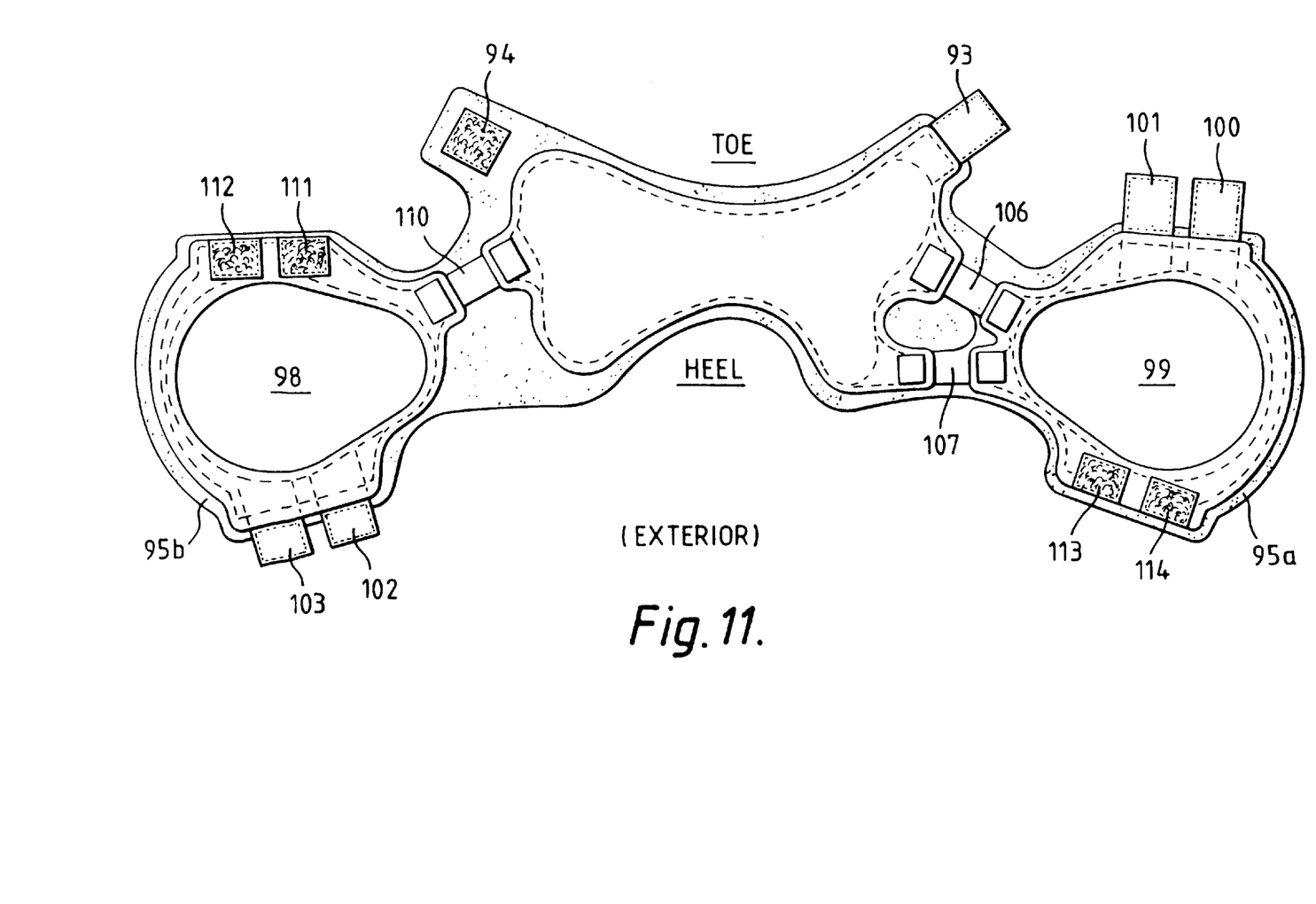
FIG. 11 is an exterior view of the brace of FIG. 10.

The brace 90 of FIGS. 10 and 11 is shown laid out flat. In use the brace 90 would be configured to extend around the lower foot and ankle of the wearer's foot.

The view of FIG. 10 shows the brace having a foot section 91 extending slightly beyond the boundary of a thermal molded plastic foot insert 92. Strap 93 corresponds to strap 35 in FIG. 4 and extends over the foot and attaches to site 94. A VELCRO fastener is employed.

The upper portion 95a, 95b of the brace has a medial anchor site 96 and a lateral anchor site 97 with pads like that shown in FIGS. 8a and 8b in contact with the skin of the wearer's foot. The exterior of these sites is covered with a VELCRO material 98, 99 to enable connections like the talar stabilizing connections and the inversion limiting connection to be made to the brace. Straps 100, 101 close off the anterior upper portion of the brace about anterior portion thereof while straps 102, 103 do likewise at a posterior portion thereof. VELCRO fasteners are used. Tabs 104, 105 provide strengthened zones relative to which elastic lateral connections 104, 107 are made. Tabs 108, 109 provide strengthened zones relative to which an elastic medial connection 110 is made.

The brace 90 consists of inner and outer layers of neoprene. At the location of anchor sites 96, 97 the layers have pear shaped apertures so that the pads 98, 99 when attached to the inner layer are visible from the outside to make the VELCRO material accessible on the outside.

VELCRO pads 111, 112 cooperate with tabs 102, 103 while VELCRO pads 113, 114 cooperate with tabs 101, 100.

The brace of the invention enables normal range of movement of the ankle. Movement beyond this range is progressively resisted to prevent injury. The pads employed at the anchor sites stimulate the ankle everting muscles to assist in preventing inversion due to stimulation of skin receptors over these muscles.

The brace prevents ligament injury to the lateral capsule of the ankle during simulated inversion sprain and is able to maintain this protection under exercise conditions without significant reduction in support.

Plantar and dorsi flexion is allowed without significant range of motion restrictions compared to normal range of motion sufficient to prevent injury. The brace allows inversion-eversion range of motion with negligible support at a neutral position and maximum support at the extent of range of motion. The brace is adjustable easily removable and re-usable. The brace allows adjustment of talar tilt at heel strike, maintains this alignment during exercise with elastic tension while allowing for natural subtalar range of motion during the stance phase of locomotion to toe-off. The brace is capable of increasing the time of loading of abnormal forces at the limit of the range of motion due to sudden inversion, transfer these forces to the lower leg and thus reduce the high impulse momentum transfer normally associated with this motion than with current rigid or semi-rigid supports.

The brace enables more normal foot ankle biomechanics by not limiting natural range of motion and is able to correct abnormal anatomical alignment. The brace provides a superiorly directed force through the calcaneus and the talus to hold the talus within the ankle mortise. The advantage of this is that it negates the effects of lax ligaments and heel tilting, required for rehabilitation and correct articular surface contact.

I claim:

1. An ankle brace having an upper portion adapted to extend about a wearer's ankle adjacent a malleoli, the upper portion having at least one anchor site, a foot section conforming to a portion of a sole of the wearer's foot and at least one elastic lateral connection extending between the foot section and the upper portion enabling a normal range of movement of the ankle and becoming increasingly taut at about the limit of at least one of the normal range of movement and a preset range of movement, at least one elastic medial connection between the foot section and the upper portion of the brace which enables the normal range of movement of the ankle and becomes increasingly taut at about the limit of at least one of the normal range of movement and a preset range of movement, a medial anchor site and a lateral anchor site on the upper portion of the brace, and adjustable talar stabilizing connections including a medial and a lateral talar stabilizing connection, the talar stabilizing connections extending from a posterior portion of the foot section, crossing over each other in the region of the Achilles tendon and to opposite superior sides of the brace and terminating at the medial and the lateral anchor sites.

2. The brace of claim 1 including two said lateral connections.

3. The brace of claim 1 including an adjustable inversion limiting connection extending from the foot section from an anterior lateral position adjacent the cuboid of the foot across the outside of the ankle joint to the medial anchor site.

4. The brace of claim 3 including an inversion limiting connection extending from the cuboid to the lateral anchor site.

5. The brace of claim 1 wherein the foot section includes a foot insert moldable to conform to the contour of the wearer's foot.

6. The brace of claim 5 wherein the foot insert has a reduced width at its lateral border and is of increased width across the instep to beneath the medial malleolus and more anteriorly to a location approximately over the talonavicular joint.

7. The brace of claim 5 including a comfort lining extending over the foot insert.

8. The brace of claim 1 wherein the upper portion completely encircles the foot of the wearer above the malleoli.

9. The brace of claim 8 wherein at least one of a posterior portion and an anterior portion of the upper portion is elastic to enable the wearer's foot to be inserted into the brace.

10. The brace of claim 8 wherein at least one of an anterior portion and a posterior portion of the upper portion of the brace is open and at least one adjustable connection is present to close the opening once the foot is inserted.

11. The brace of claim 10 wherein the upper portion is open both anteriorly and posteriorly and two said adjustable connections close off both the anterior and posterior portions of the upper portions of the brace.

12. The brace of claim 1 wherein the elastic medial and lateral connections are straps and have fixotropic characteristics.

13. The brace of claim 1 wherein the anchor sites are located above each malleoli.

14. The brace of claim 13 wherein the anchor sites are located below the interior of the triceps surae.

15. The brace of claim 1 wherein the anchor sites include a pad in contact with the foot and having suction pads.

16. The brace of claim 1 wherein the anchor sites include a pad made of synthetic material which conforms to the contour of the foot.

17. An ankle brace having an upper portion adapted to extend about a wearer's ankle above a malleoli, the upper portion having at least one anchor site which directly contacts skin of the wearer's foot, a foot section conforming to a portion of a sole of the wearer's foot and at least one elastic lateral connection extending between the foot section and the upper portion enabling a normal range of movement of the ankle and becoming increasingly taut at about the limit of at least one of the normal range of movement and a preset range of movement, said at least one anchor site having means for adhering the upper portion in a region of the anchor site to the skin of the wearer's foot.

18. The brace of claim 17 wherein the anchor site includes a pad in contact with the skin of the wearer's foot and the means for adhering comprise an adhesive applied to said pad.

19. The brace of claim 18 wherein the pad is made of synthetic material which conforms to the contour of the foot.

20. The brace of claim 17 wherein the anchor site includes a pad in contact with the skin of the wearer's foot and the means for adhering comprises a number of openings formed in a surface of the pad adjacent the skin of the wearer's foot, said openings allowing the wearer's skin to conform therewith to provide said adhering to the wearer's skin.

21. The brace of claim 20 wherein the means for adhering further comprises an adhesive applied to said pad.

22. The brace of claim 20 wherein the pad is made of synthetic material which conforms to the contour of the foot.

23. The brace of claim 17 wherein the anchor site includes a pad in contact with the skin of the wearer's foot and the means for adhering comprises a number of suction cups on said pad.

24. The brace of claim 23 wherein the pad is made of synthetic material which conforms to the contour of the foot.

25. The brace of claim 17 including two said lateral connections.

26. The brace of claim 17 or 25 including a medial anchor site and a lateral anchor site on the upper portion of the brace.

27. The brace of claim 26 including an adjustable inversion limiting connection extending from the foot section from an anterior lateral position adjacent a cuboid of the foot across the outside of the ankle joint to the medial anchor site.

28. The brace of claim 27 including an inversion limiting connection extending from the cuboid to the lateral anchor site.

29. The brace of claim 26 including adjustable talar stabilizing connections including a medial talar stabilizing connection and a lateral talar stabilizing connection, the talar stabilizing connections extending from a posterior portion of the foot section, crossing over each other in the region of the Achilles tendon and to opposite superior sides of the brace and terminating at the medial and the lateral anchor sites.

30. The brace of claim 29 wherein the talar stabilizing connections are straps having elastic characteristics.

31. The brace of claim 29 wherein the talar stabilizing connections are of adjustable length.

32. The brace of claim 26 wherein the anchor sites are located below the inferior of the triceps surae.

33. The brace of claim 17 or 25 further comprising at least one elastic medial connection between the foot section and the upper portion of the brace which enables the normal range of movement of the ankle and becomes increasingly taut at about the limit of at least one of the normal range of movement and a preset range of movement, wherein the elastic medial connection and the elastic lateral connection are straps and have fixotropic characteristics.

34. The brace of claim 17 wherein the foot section includes a foot insert moldable to conform to the contour of the wearer's foot.

35. The brace of claim 34 wherein the foot insert has a reduced width at its lateral border and is of increased width across the instep to beneath the medial malleolus and more anteriorly to a location approximately over the talonavicular joint.

36. The brace of claim 34 including a comfort lining extending over the foot insert.

37. The brace of claim 17 wherein the upper portion completely encircles the foot of the wearer above the malleoli.

38. The brace of claim 37 wherein at least one of a posterior portion and an anterior portion of the upper portion is elastic to enable the wearer's foot to be inserted into the brace.

39. The brace of claim 37 wherein at least one of an anterior portion and a posterior portion of the upper portion of the brace is open and at least one adjustable connection is present to close the opening once the foot is inserted.

40. The brace of claim 39 wherein the upper portion is open both anteriorly and posteriorly and two said adjustable connections close off both the anterior and posterior portions of the upper portions of the brace.

* * * * *